(12) United States Patent
Kunesh

(10) Patent No.: US 9,248,210 B2
(45) Date of Patent: Feb. 2, 2016

(54) DUAL PURPOSE CARTRIDGE DISPENSING SYSTEM

(75) Inventor: Edward J. Kunesh, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 13/586,759

(22) Filed: Aug. 15, 2012

(65) Prior Publication Data

US 2014/0048545 A1 Feb. 20, 2014

(51) Int. Cl.
  *A61L 9/12* (2006.01)
  *G09F 1/12* (2006.01)
  *A47G 1/14* (2006.01)
  *A01M 1/20* (2006.01)

(52) U.S. Cl.
  CPC .............. *A61L 9/12* (2013.01); *A01M 1/2055* (2013.01); *A47G 1/141* (2013.01); *A61L 2209/133* (2013.01)

(58) Field of Classification Search
  CPC ......... A61L 9/12; A61L 9/04; A61L 2209/15; A61L 2209/13; A61L 2209/133; A47G 1/141; A47G 1/0616; A01M 1/2055
  USPC ............... 220/359.1; 40/755, 124.15, 124.09, 40/725, 756, 789, 124.19, 152, 774, 777, 40/642, 750, 748, 406, 407; 239/34, 53, 239/55, 56, 60, 58; 206/462, 0.5, 737, 779, 206/467, 45.24, 583; 229/71, 92; 428/905
  See application file for complete search history.

(56) References Cited

U.S. PATENT DOCUMENTS

| | | | | |
|---|---|---|---|---|
| 481,173 A | * | 8/1892 | Heymann | 40/1 |
| 849,111 A | | 4/1907 | Fairchild | |
| 868,998 A | * | 10/1907 | Lang | 248/465 |
| 1,486,652 A | * | 3/1924 | Froelich | 40/750 |
| 1,532,290 A | * | 4/1925 | Wilson | 40/124.15 |
| 1,581,912 A | * | 4/1926 | Born | 40/755 |
| 1,679,083 A | * | 7/1928 | Helmquest | 40/756 |
| 1,711,199 A | | 4/1929 | Hatch | |
| 2,431,835 A | * | 12/1947 | Smith | 40/124.15 |
| 2,577,320 A | * | 12/1951 | Fenyo | B44F 7/00 101/171 |
| 2,600,429 A | * | 6/1952 | Ranseen | 40/661.08 |
| 2,626,833 A | * | 1/1953 | Valentine | 239/56 |

(Continued)

FOREIGN PATENT DOCUMENTS

| | | |
|---|---|---|
| EP | 423816 | 4/1991 |
| EP | 722743 | 7/1996 |

(Continued)

OTHER PUBLICATIONS

Glade Decor Scents Flass Holder, web page, <http://www.glade.com/en-US/Products/Pages/decor-scents.aspx>.

(Continued)

*Primary Examiner* — Mickey Yu
*Assistant Examiner* — Gideon Weinerth

(57) ABSTRACT

A package for a refill for dispensing a volatile material is disclosed that includes a wall portion and a cartridge refill removably attached to the wall portion. Attachment means removably attach the cartridge refill to the wall portion. The package in a first state is substantially planar in structure. The cartridge refill may be removed from the package for use in a separate dispenser or the package may be used as a dispenser for the volatile material held within the cartridge refill.

14 Claims, 16 Drawing Sheets

(56) References Cited

U.S. PATENT DOCUMENTS

| | | | |
|---|---|---|---|
| 2,878,061 A * | 3/1959 | Saeks | 239/60 |
| 3,033,357 A | 5/1962 | Vogel | |
| 3,072,247 A | 1/1963 | Fielding | |
| 3,093,244 A * | 6/1963 | Middleton, Jr. | B65D 75/36 206/45.24 |
| 3,127,010 A * | 3/1964 | Capezzuto | B65D 75/368 206/214 |
| 3,174,244 A * | 3/1965 | Walton | 40/774 |
| 3,249,217 A * | 5/1966 | Irving | B65D 75/36 206/461 |
| 3,352,409 A * | 11/1967 | Link | B65D 75/30 206/463 |
| 3,382,970 A | 5/1968 | Sellors | |
| 3,424,380 A * | 1/1969 | Curran | 239/60 |
| 3,455,440 A | 7/1969 | West | |
| 3,521,816 A * | 7/1970 | Wilson | A01M 1/2055 239/60 |
| 3,544,007 A * | 12/1970 | Bordman | 239/60 |
| 3,557,945 A * | 1/1971 | Gourio | A47F 3/14 206/45.24 |
| 3,613,994 A * | 10/1971 | Goodman | A01M 1/2044 206/0.5 |
| 3,820,262 A | 6/1974 | Dewsnap | |
| 3,990,578 A | 11/1976 | Roeser | |
| 4,032,005 A | 6/1977 | Vereb | |
| 4,083,447 A | 4/1978 | Walters et al. | |
| 4,227,640 A | 10/1980 | Roccaforte | |
| 4,240,552 A | 12/1980 | Brown | |
| 4,285,468 A * | 8/1981 | Hyman | A01M 1/2044 239/55 |
| 4,523,870 A | 6/1985 | Spector | |
| 4,634,614 A * | 1/1987 | Holzner | A61L 9/042 206/484.1 |
| 4,660,763 A | 4/1987 | Gutkowski et al. | |
| 4,702,368 A * | 10/1987 | Jones | B65D 75/36 206/45.24 |
| D293,861 S * | 1/1988 | Harwood | D6/311 |
| 4,739,928 A | 4/1988 | O'Neil | |
| 4,780,975 A * | 11/1988 | Friedman | 40/755 |
| 4,804,142 A * | 2/1989 | Riley | A01M 29/12 239/56 |
| 4,813,902 A * | 3/1989 | Messer | 446/71 |
| 4,814,212 A | 3/1989 | Spector | |
| 4,883,692 A * | 11/1989 | Spector | 428/16 |
| 4,993,177 A * | 2/1991 | Hudson | 40/725 |
| 5,230,867 A * | 7/1993 | Kunze et al. | 422/123 |
| 5,361,522 A * | 11/1994 | Green | 40/725 |
| 5,383,598 A * | 1/1995 | Styles | A61L 9/12 239/34 |
| 5,395,047 A * | 3/1995 | Pendergrass, Jr. | 239/56 |
| 5,439,100 A * | 8/1995 | Gordon et al. | 206/5 |
| D366,107 S * | 1/1996 | Shaffer | D23/366 |
| 5,480,591 A | 1/1996 | Lagneaux et al. | |
| 5,518,790 A * | 5/1996 | Huber | A61L 9/12 206/484 |
| 5,527,493 A | 6/1996 | McElfresh et al. | |
| 5,611,486 A | 3/1997 | Paul | |
| 5,711,101 A | 1/1998 | Mueller et al. | |
| 5,788,061 A | 8/1998 | Hammond | |
| 5,885,701 A * | 3/1999 | Berman | A45D 40/0087 156/276 |
| D407,809 S * | 4/1999 | Hammond | D23/366 |
| 5,901,844 A | 5/1999 | Gambardella et al. | |
| 5,911,358 A | 6/1999 | Kenner et al. | |
| 5,961,043 A * | 10/1999 | Samuelson et al. | 239/54 |
| 5,975,427 A * | 11/1999 | Harries | 239/34 |
| 6,282,828 B1 | 9/2001 | Cecchetto | |
| 6,386,971 B1 | 5/2002 | Johnson | |
| 6,615,986 B2 * | 9/2003 | Pirro | B65D 73/0092 206/459.5 |
| 6,643,967 B1 * | 11/2003 | Bloom | 40/789 |
| 6,691,870 B1 * | 2/2004 | Palm et al. | 206/462 |
| 6,713,024 B1 | 3/2004 | Arnell et al. | |
| 6,746,051 B1 | 6/2004 | Archie, Jr. et al. | |
| 6,749,672 B2 | 6/2004 | Lynn | |
| 6,871,430 B1 * | 3/2005 | Landolt | 40/124.12 |
| 7,175,815 B2 | 2/2007 | Yamasaki et al. | |
| 7,182,305 B2 | 2/2007 | Dempsey | |
| 7,188,780 B2 * | 3/2007 | Martens, III | A61L 9/04 206/484.1 |
| 7,213,770 B2 * | 5/2007 | Martens et al. | 239/57 |
| 7,331,485 B2 * | 2/2008 | Peterson et al. | 222/78 |
| 7,426,799 B2 * | 9/2008 | Christianson et al. | 40/725 |
| 7,441,360 B2 * | 10/2008 | Christianson et al. | 40/725 |
| 7,475,507 B2 * | 1/2009 | Graves | 40/725 |
| 7,523,577 B2 * | 4/2009 | Majerowski | 40/768 |
| 7,527,235 B2 | 5/2009 | Hummel | |
| 7,530,503 B2 * | 5/2009 | Caserta et al. | 239/57 |
| 7,607,250 B2 * | 10/2009 | Leonard | 40/725 |
| D607,984 S | 1/2010 | Ko et al. | |
| 7,651,763 B2 | 1/2010 | Hutchings et al. | |
| 7,665,238 B2 * | 2/2010 | Majerowski | 40/725 |
| 7,988,073 B2 | 8/2011 | Ligney et al. | |
| 8,286,894 B2 * | 10/2012 | Moreno Perez et al. | 239/6 |
| 8,684,182 B2 * | 4/2014 | Bailey | B65D 73/0092 206/45.24 |
| 2003/0085297 A1 * | 5/2003 | Huang | 239/34 |
| 2003/0200690 A1 * | 10/2003 | Galloway | 40/779 |
| 2004/0000596 A1 | 1/2004 | Cuthbert | |
| 2004/0256480 A1 * | 12/2004 | Channer | A01M 1/14 239/34 |
| 2005/0150973 A1 * | 7/2005 | Brown | A01M 1/2044 239/6 |
| 2006/0000920 A1 * | 1/2006 | Leonard | A61L 9/12 239/34 |
| 2006/0002102 A1 | 1/2006 | Leonard | |
| 2006/0032937 A1 * | 2/2006 | Caserta | A01M 1/2044 239/34 |
| 2006/0118583 A1 | 6/2006 | Christianson et al. | |
| 2007/0057086 A1 * | 3/2007 | Van Kippersluis | A61L 9/04 239/43 |
| 2007/0187264 A1 | 8/2007 | Hofte et al. | |
| 2007/0194368 A1 * | 8/2007 | Caserta et al. | 257/315 |
| 2007/0251131 A1 * | 11/2007 | Majerowski | A01M 1/2055 40/407 |
| 2007/0262166 A1 * | 11/2007 | Majerowski | A01M 1/2055 239/57 |
| 2008/0216374 A1 * | 9/2008 | Ozmun | A47G 1/0605 40/723 |
| 2008/0237330 A1 | 10/2008 | Grossmann et al. | |
| 2009/0123344 A1 * | 5/2009 | Dobler | A61L 9/12 422/123 |
| 2009/0145015 A1 | 6/2009 | Graves | |
| 2014/0027530 A1 * | 1/2014 | Cao | A61L 9/042 239/6 |
| 2015/0021408 A1 * | 1/2015 | Matthews | A61L 9/12 239/34 |

FOREIGN PATENT DOCUMENTS

| | | | | |
|---|---|---|---|---|
| EP | 1082970 A1 | 3/2001 | | |
| EP | 1645294 | 4/2006 | | |
| GB | 2053836 A * | 2/1981 | | B65D 75/36 |
| JP | 9084863 | 3/1997 | | |
| JP | 10263068 | 10/1998 | | |
| JP | 11042150 | 2/1999 | | |
| JP | 2004182312 A | 7/2004 | | |
| JP | 2010263068 | 11/2010 | | |
| JP | 11042150 | 3/2011 | | |
| JP | 2011087880 | 5/2011 | | |
| WO | 00/00020 A1 | 1/2000 | | |
| WO | 2009/002435 A2 | 12/2008 | | |
| WO | 2010/112895 | 10/2010 | | |

OTHER PUBLICATIONS

Volkswagen Air Freshener, web page, <http://productdesigner.co.uk/portfoliovw.html>.

Renuzit New Fresh Accents, web page, <http://www.renuzit.com/products/after-the-rain-fresh-accents/>.

(56) References Cited

OTHER PUBLICATIONS

Renuzit Fresh Accents Holiday Air Freshener, web page, <http://www.nancysfreeselections.blogspot.in/2011/10/giveaway-renuzit-fresh-accents-hoiday.html>.

Cherry Pie—Air Freshener, web page, <http://www.neatoshop.com/product/Cherry-Pie-Air-Freshener>.

Foto Fresh Wallet Size Picture Frame Air Freshener, web page, <http://amazon.com/Wallet-Picture-Frame-Freshener-Hawaiian/dp/B005E197DG/ref=sr_1_1?ic=UTF8&qid=1335558916&sr=8-1>.

Frame-A-Pet Air Fresheners, web page, <http://crazydog.com/products/products_funstuff.htm>.

PCT/US2013/055044 International Search Report dated Nov. 12, 2013.

* cited by examiner

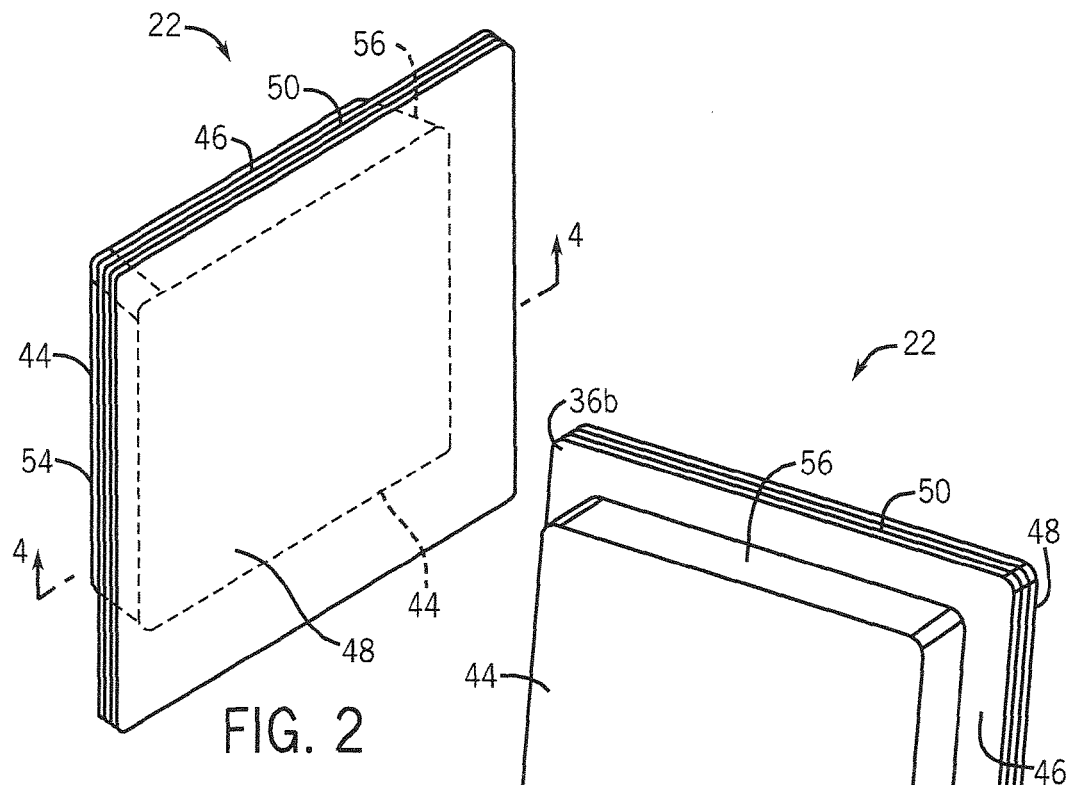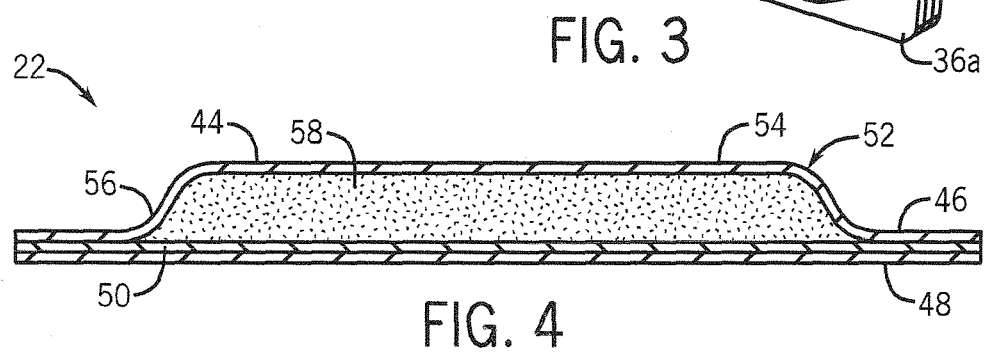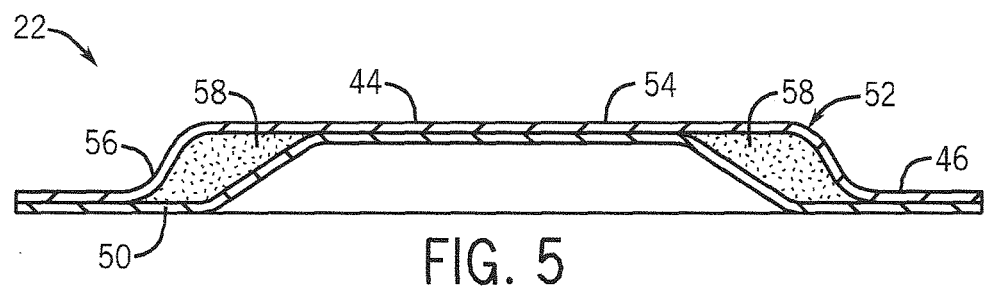

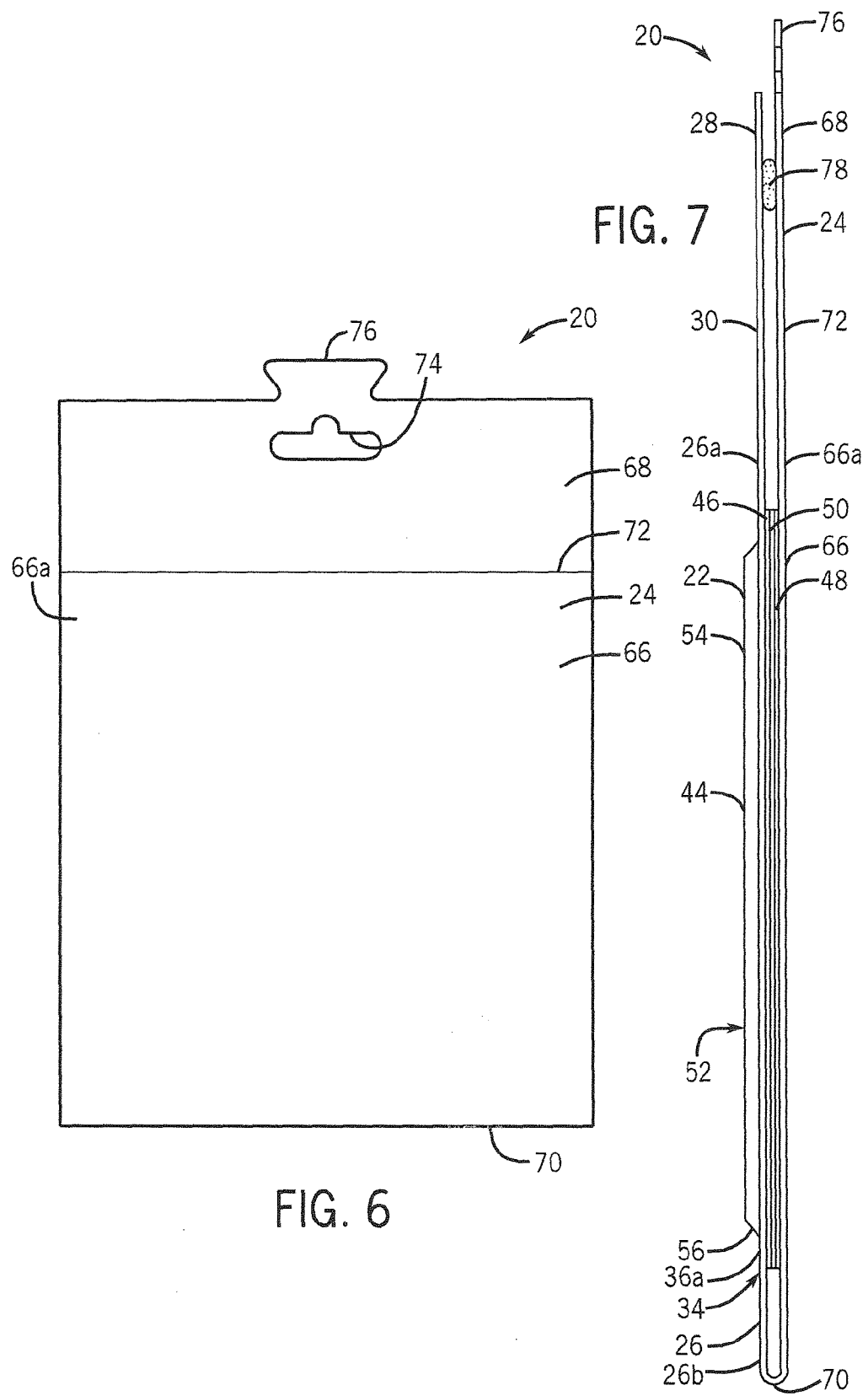

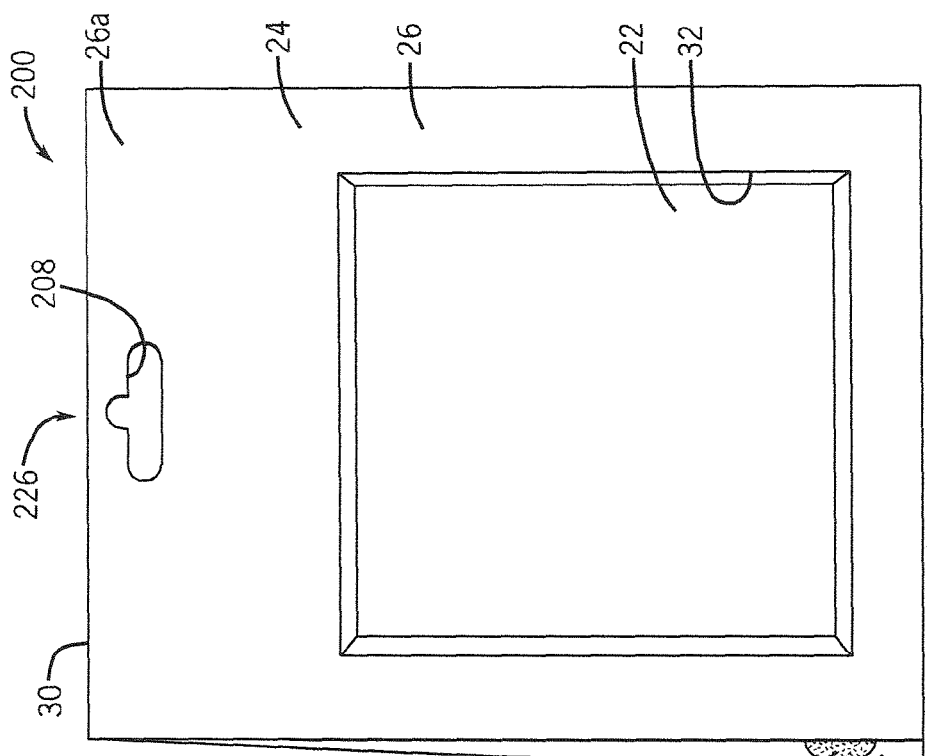
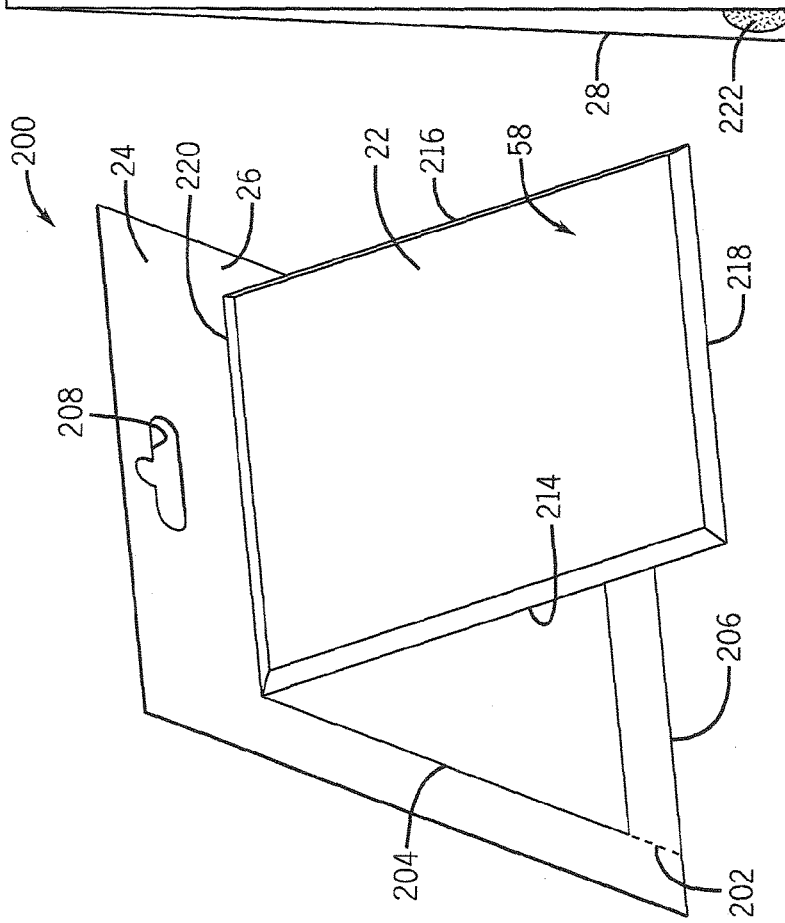

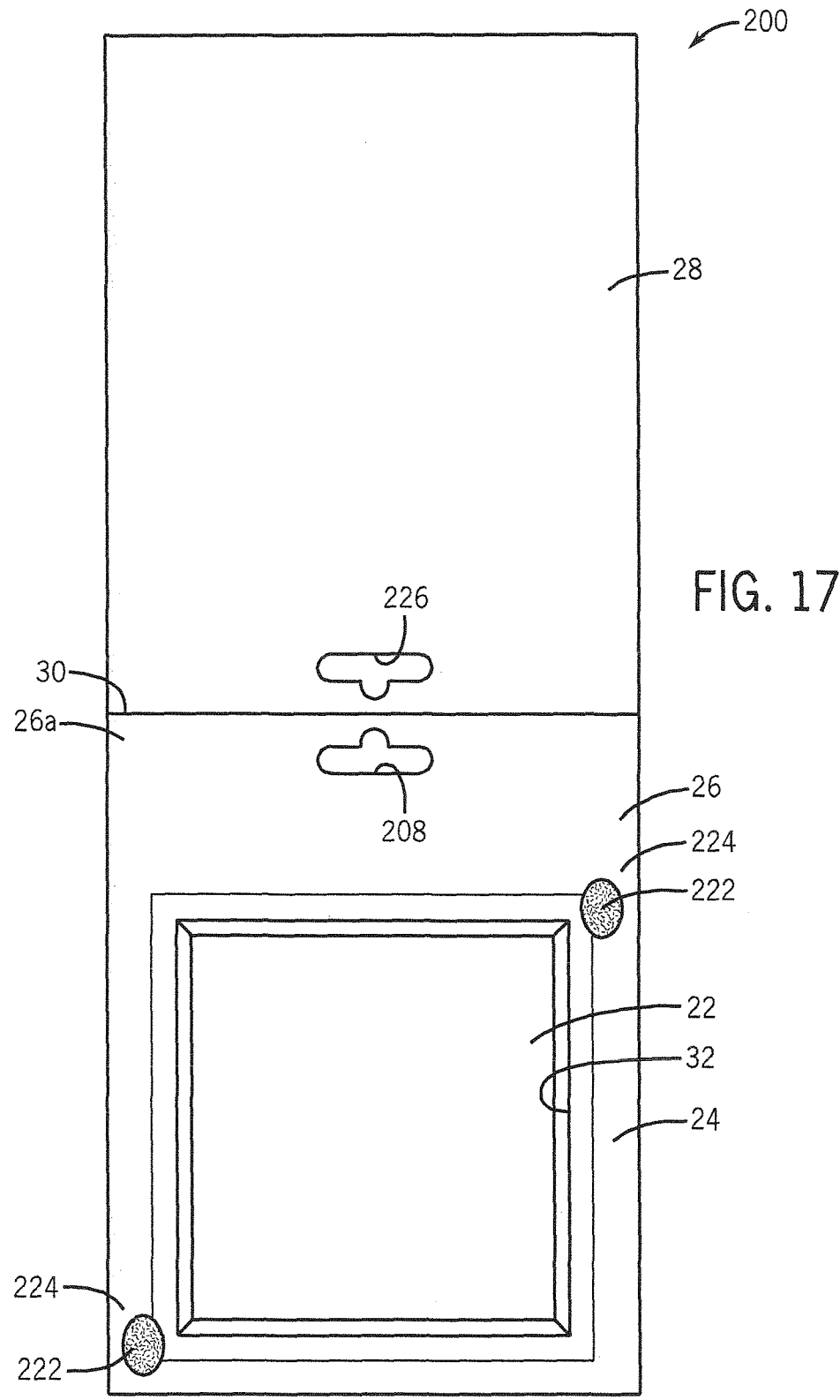

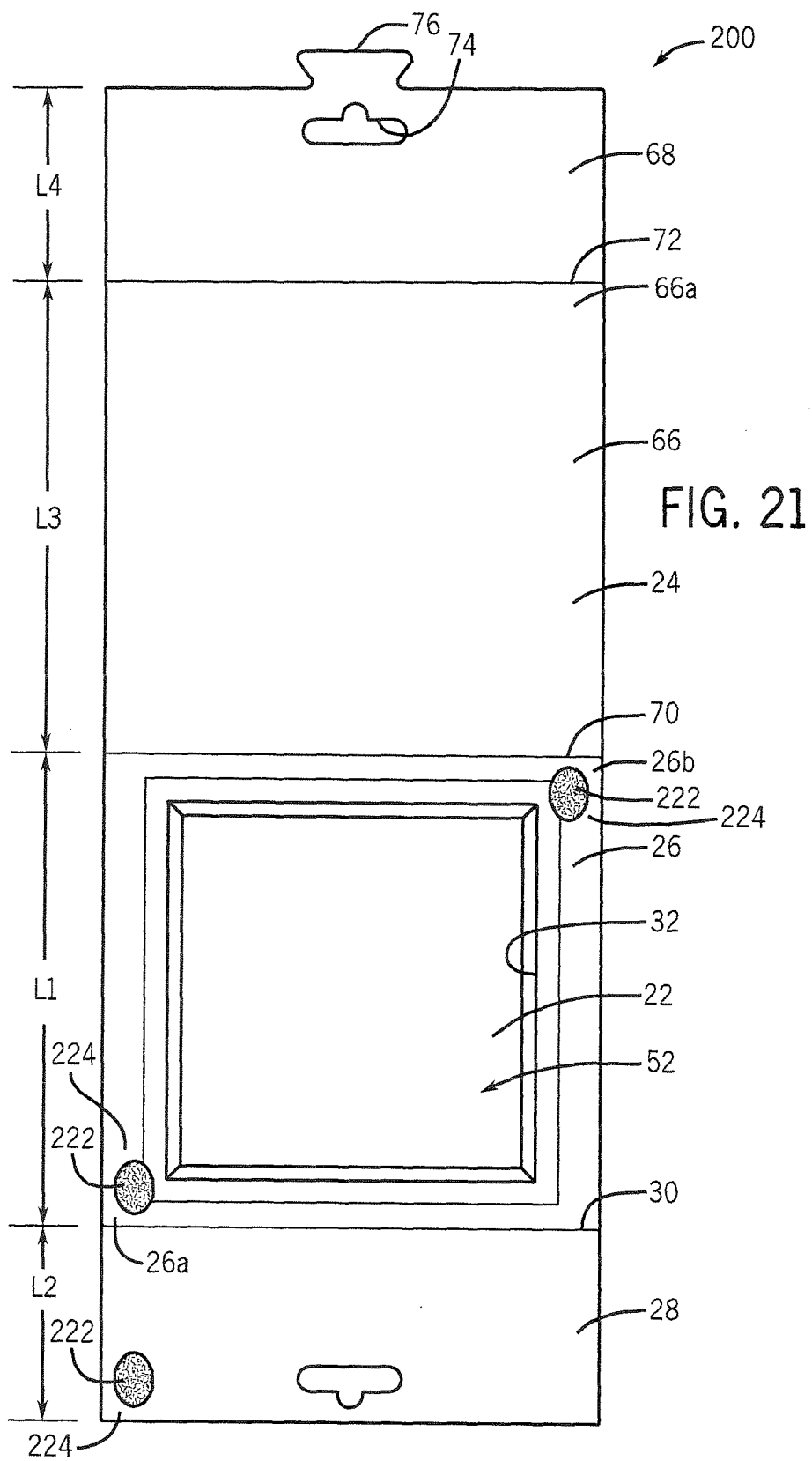

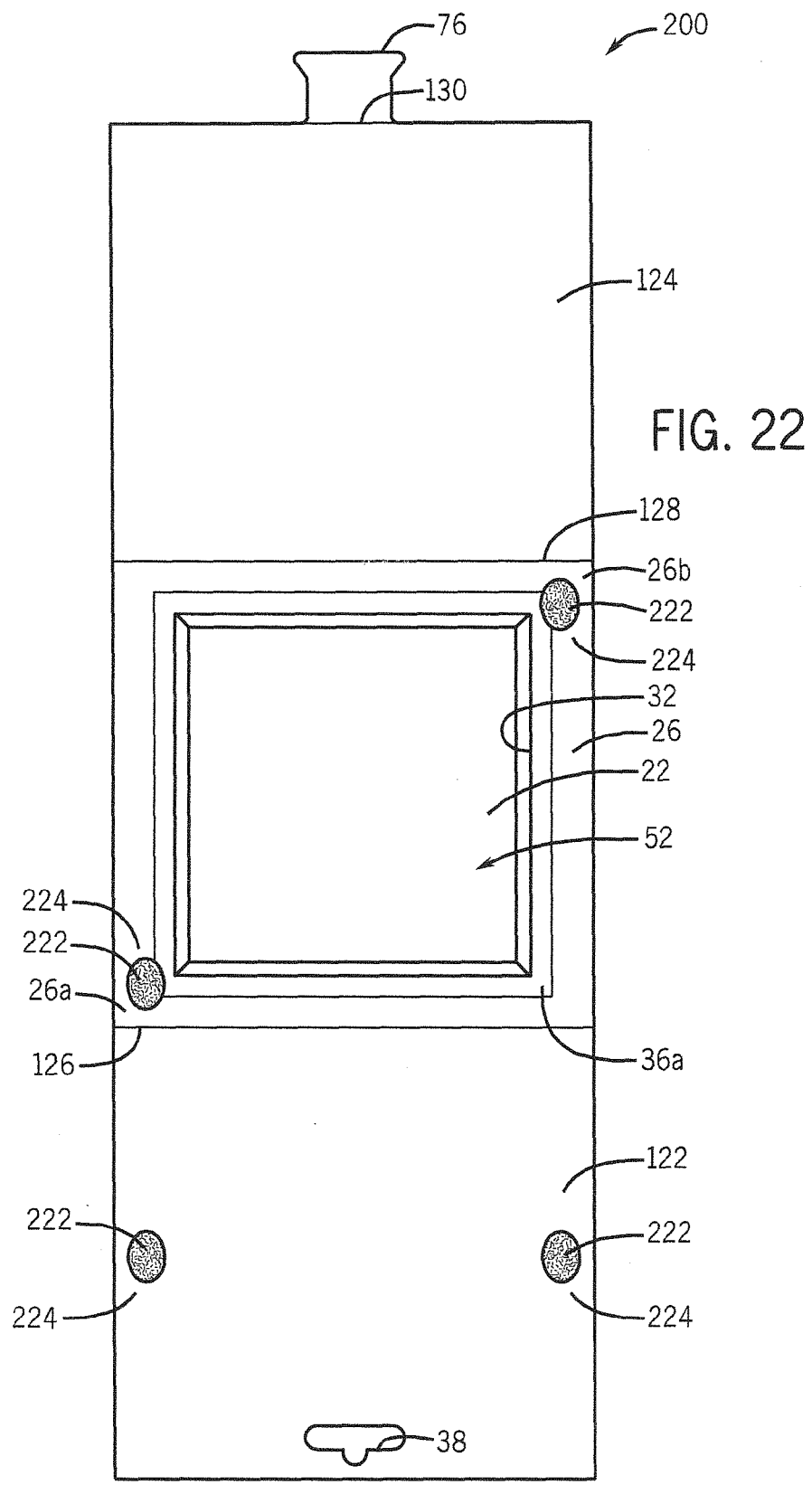

DUAL PURPOSE CARTRIDGE DISPENSING SYSTEM

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispensing system, and more particularly, to a volatile material dispenser in combination with an adjustable chipboard holder.

2. Description of the Background

Volatile material dispensers have been used to provide fragrances to office or home settings. One such dispenser is an ornamental design for a combined picture frame and potpourri holder. The design includes front and rear panels angled from each other. A recess is centered within the front panel to provide an area to insert a photograph. A bridge connects both the front and rear panels.

Another such ornamental design for a dispenser includes a combined air freshener and picture frame. The frame includes front and rear faces, wherein the front face includes two rectangular stepped portions extending outwardly therefrom and the rear face is planar. An opening extends through the front and rear faces adjacent an upper portion of the frame.

Yet another dispenser includes first and second panels. A base joins the first and second panels to provide a platform to support the device in a tent configuration. The second side panel has a tab extending therefrom. Means are provided to capture the tab that is associated with the first side panel. An opening in one of the side panels is provided for mounting a volatile material filled reservoir.

One device that has been adapted to discharge a volatile material includes a display frame having a front face and a rear face with an opening disposed in the front face. The device further includes a dispenser disposed within the display frame. The dispenser includes a blister that holds a volatile material and a permeable membrane that extends across an open end of the blister. The rear face includes an integral foot member actuable between first and second states. The permeable membrane is disposed adjacent the front face and prevents the release of the volatile material in a first condition and permits the release of the volatile material through the opening in a second condition.

Another device that has been adapted to discharge a volatile material includes a display frame having a front face and a rear face and an opening disposed in the rear face. The device further includes a dispenser disposed within the display frame. The dispenser includes a blister that holds a volatile material and a permeable membrane that extends across an open end of the blister. The rear face includes an integral foot member connected to an upper portion of the display frame at a hinge and the integral foot member is actuable between first and second states about the hinge. Further, the permeable membrane is disposed adjacent the rear face and regulates release of the volatile material therethrough.

SUMMARY OF THE INVENTION

According to one embodiment, a package for a refill for dispensing a volatile material includes a first wall portion, a cartridge refill removably attached to the first wall portion, a second wall portion hingedly connected to a first end of the first wall portion about a first fold line, and attachment means that at least one of removably attach the cartridge refill to the first wall portion and removably attach the first wall portion to the second wall portion. The first wall portion, the cartridge refill, and the second wall portion form a substantially planar structure in a first state. In a second state the first wall portion and the second wall portion rotate about the first fold line to create a substantially non-planar structure that enables a user to detach the cartridge refill from the first wall portion or utilize the package as a display frame to facilitate dispensing a volatile material from the cartridge refill.

According to another embodiment, a package for a refill for dispensing a volatile material includes a first wall portion with an opening disposed therein, a cartridge refill removably disposed within the opening, and a second wall portion hingedly connected to a first end of the first wall portion about a first fold line. The first wall portion, the cartridge refill, and the second wall portion form a substantially planar structure in a first state. In a second state the first wall portion and the second wall portion rotate about the first fold line to create a substantially non-planar structure that enables a user to remove the cartridge refill from the opening or utilize the package as a display frame to facilitate dispensing a volatile material from the cartridge refill.

According to yet another embodiment, a package for a refill for dispensing a volatile material includes a wall portion with an opening disposed therein, a cartridge refill disposed within the opening, and attachment means that removably attach the cartridge refill to the wall portion. The wall portion and the cartridge refill form a substantially planar structure in a first state. Partial disruption of the attachment means partially removes the cartridge refill from the wall portion to create a substantially non-planar structure in a second state to facilitate dispensing a volatile material from the cartridge refill.

BRIEF DESCRIPTION OF THE DRAWINGS

Other aspects and advantages of the present invention will become apparent upon reading the following detailed description and upon reference to the drawings in which:

FIG. 2 is a front isometric view of the dispenser of FIG. 1;

FIG. 3 is a rear isometric view of the dispenser of FIG. 1;

FIG. 4 is a cross-sectional view of the dispenser of FIG. 2 along the lines 4-4 in a first condition;

FIG. 5 is a cross-sectional view of the dispenser of FIG. 2, similar to FIG. 4, showing the dispenser in a second condition;

FIG. 6 is a rear elevational view of the dispensing system of FIG. 1;

FIG. 7 is a side elevational view of the dispensing system of FIG. 1;

FIG. 15 is a front isometric view of the package of FIG. 12 in a second state;

FIG. 16 is a front elevational view of a package for a cartridge refill according to a second embodiment;

FIG. 17 is a bottom plan view of the package of FIG. 16 in an unfolded state;

FIG. 21 is a plan view of a package in an unfolded state similar to the dispensing system of FIG. 9; and FIG. 22 is a plan view of a package in an unfolded state similar to the dispensing system of FIG. 10.

DETAILED DESCRIPTION OF THE INVENTION

Figure 1:
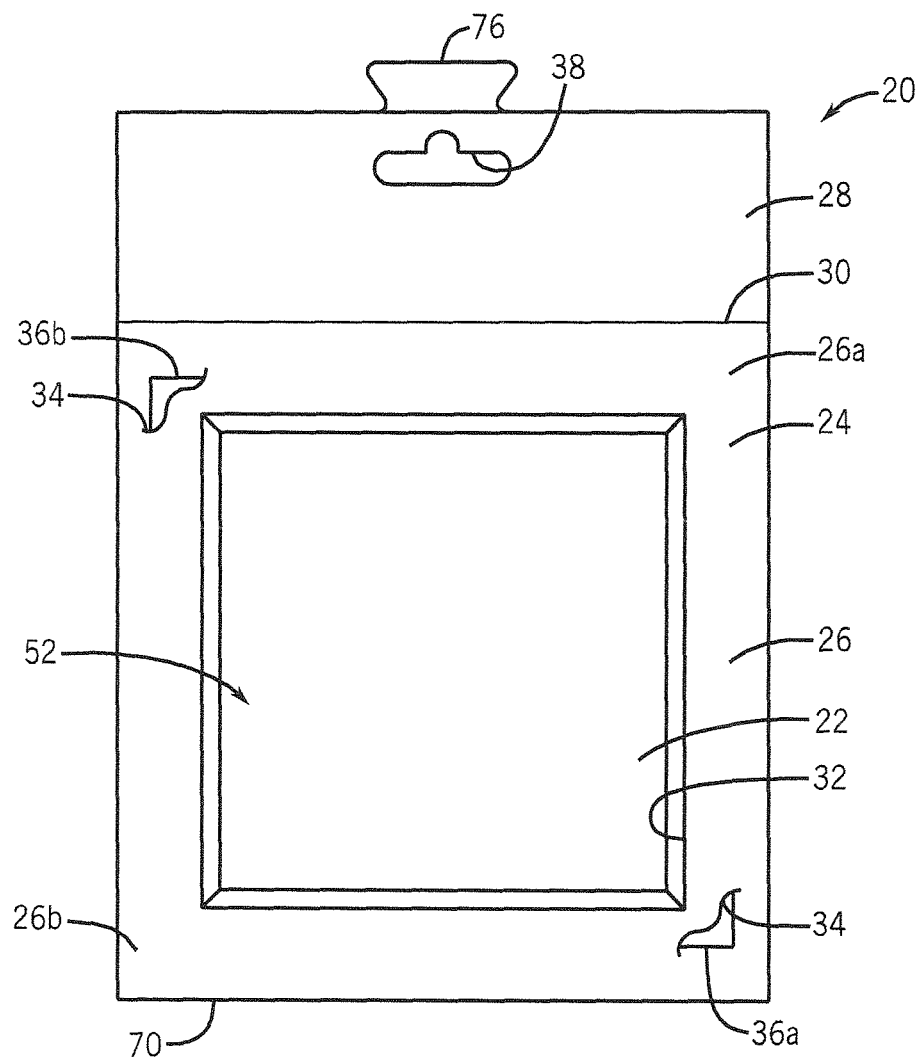
FIG. 1 is a front elevational view of a dispensing system in a first state that includes a frame and a dispenser.

Referring to FIG. 1, a volatile material dispensing system 20 is illustrated. The dispensing system 20 includes a volatile material dispenser 22 and a display frame 24. The dispensing system 20 is foldable between a first state (shown) where the system is substantially planar or flat and a second state, which is substantially triangular (see FIG. 8). The display frame 24 comprises a first wall portion 26 and a second wall portion 28 hingedly attached to a first end 26a of the first wall portion 26 by a first fold line 30. The first wall portion 26 may be substantially rectangular in shape. An opening 32 is disposed within the first wall portion 26. The first wall portion 26 further includes at least two arcuately shaped slits 34 positioned on opposite corners of the opening 32. Corner portions 36a, 36b of the dispenser 22 may be inserted into the slits 34 to releasably secure the dispenser 22 within the opening 32. In other embodiments the dispenser 22 is fittingly retained within the slits 34 or otherwise adhered or affixed to the frame 24 so as not to be removable. The second wall portion 28 includes an aperture 38 shaped to permit the dispensing system to be hung, for example, from a wall hanger display.

The dispenser 22 is further illustrated in FIGS. 2-5. With reference to FIGS. 2 and 3, the dispenser 22 or cartridge comprises a blister 44, a peripheral flange 46, and an impermeable laminate 48 releasably adhered to the blister 44 and the flange 46. The blister 44 includes a non-porous permeable membrane 50 and a cup-shaped structure 52 or reservoir. The cup-shaped structure 52 includes a bottom wall 54 and four side walls 56 that in conjunction with the permeable membrane 50 act as a sealed reservoir to contain a volatile material 58 (shown in FIGS. 4 and 5). Illustratively, the cup-shaped structure 52 and the permeable membrane 50 are formed from clear and/or translucent materials, thereby allowing the volatile material 58 to be visible therethrough. The peripheral flange 46 is planar and is coupled to and extends outwardly from top edges of the cup-shaped structure 52. In one embodiment, the peripheral flange 46 extends outwardly from upper edges of the side walls 56 and is integrally formed therewith.

The present dispenser 22 and the volatile material 58 are similar to those described in U.S. Pat. Nos. 7,213,770, 7,523, 577, and 7,665,238.

FIG. 4 illustrates the dispenser 22 in a first condition. The dispenser 22 is completely or substantially full in the first condition, i.e., little or no volatile material 58 has diffused through the permeable membrane 50 because the impermeable laminate 48 has not been removed from the blister 44. There is substantially no diffusion of the volatile material 58 when the dispenser 22 is filled and the impermeable laminate 48 covers the permeable membrane 50. Illustratively, the impermeable laminate 48 is removed from the blister 44 by a user grasping an end of the impermeable laminate 48 and peeling it off the blister 44. A tab, extension, or other means for grasping may be included as an extension of the impermeable laminate 48 to aid in removal of same. The extension may be at the corners, ends, and/or on the surface of the impermeable laminate 48.

Following removal of the impermeable laminate 48, the dispenser 22 begins to transition from a full or first condition (FIG. 4) to an empty or second condition (FIG. 5). There may be a small amount of the volatile material 58 that remains in the blister 44 and the dispenser 22 will still be considered to have reached the second condition. As the volatile material 58 diffuses through the permeable membrane 50, the permeable membrane 50 slowly collapses upon the bottom wall 54. With reference to FIG. 5, following diffusion of the volatile material 58 across the permeable membrane 50 there is less volatile material 58 contained within the dispenser 22. Substantially no new air enters the dispenser 22 subsequent to diffusion of the volatile material 58. The result of this is a pressure gradient across the permeable membrane 50, with a higher pressure existing in the ambient air than the pressure in the dispenser 22. The pressure gradient causes the ambient air to exert a net positive pressure upon the dispenser 22, which presses the permeable membrane 50 against the remaining volatile material 58 and ultimately the bottom wall 54.

Referring to FIG. 6, a rear view of the display frame 24 is depicted, where third and fourth wall portions 66, 68, respectively, may be seen. The third wall portion 66 is substantially rectangular in shape and dimensioned substantially the same as the first wall portion 26. The third wall portion 66 is integrally connected to a second end 26b of the first wall portion 26 along a second fold line 70 (see FIG. 1). Referring again to FIG. 6, an end 66a of the third wall portion 66 is connected to the fourth wall portion 68 along a third fold line 72. The fourth wall portion 68 includes an aperture 74 dimensioned substantially the same as the aperture 38 in the second wall portion 28. Further, the fourth wall portion 68 includes a tab 76 that is adapted to releasably fit within the aperture 38 and retain the tab 76 therein to hold the dispensing system in a second state (see FIG. 8).

FIG. 7 illustrates a side view of the dispensing system 20 in the first state. When the dispensing system 20 is in the first state, the frame 24 is folded about the second fold line 70 so that the first 26 and third 66 wall portions and the second 28 and fourth 68 wall portions, respectively, are aligned substantially uniformly. Prior to use, the dispensing system 20 may be suspended by means of a hanger through the apertures 38 and 74 (not shown), for example, in a wall hanger display. When hanging on a wall hanger display, the dispensing system 20 may be held in the first state by an impediment 78, such as an adhesive or staple or any other chemical or mechanical based attachment means known to one of skill in the art. A user may convert the dispensing system 20 from the first state to the second state by initially breaking the bond or otherwise removing the impediment 78 to allow the first wall portion 26 and the third wall portion 66 to rotate away from each other about the second fold line (or hinge) 70. At this point, the user gains access to the impermeable membrane 48 of the dispenser 22 to facilitate its removal and the activation of the dispensing system 20.

Figure 8:
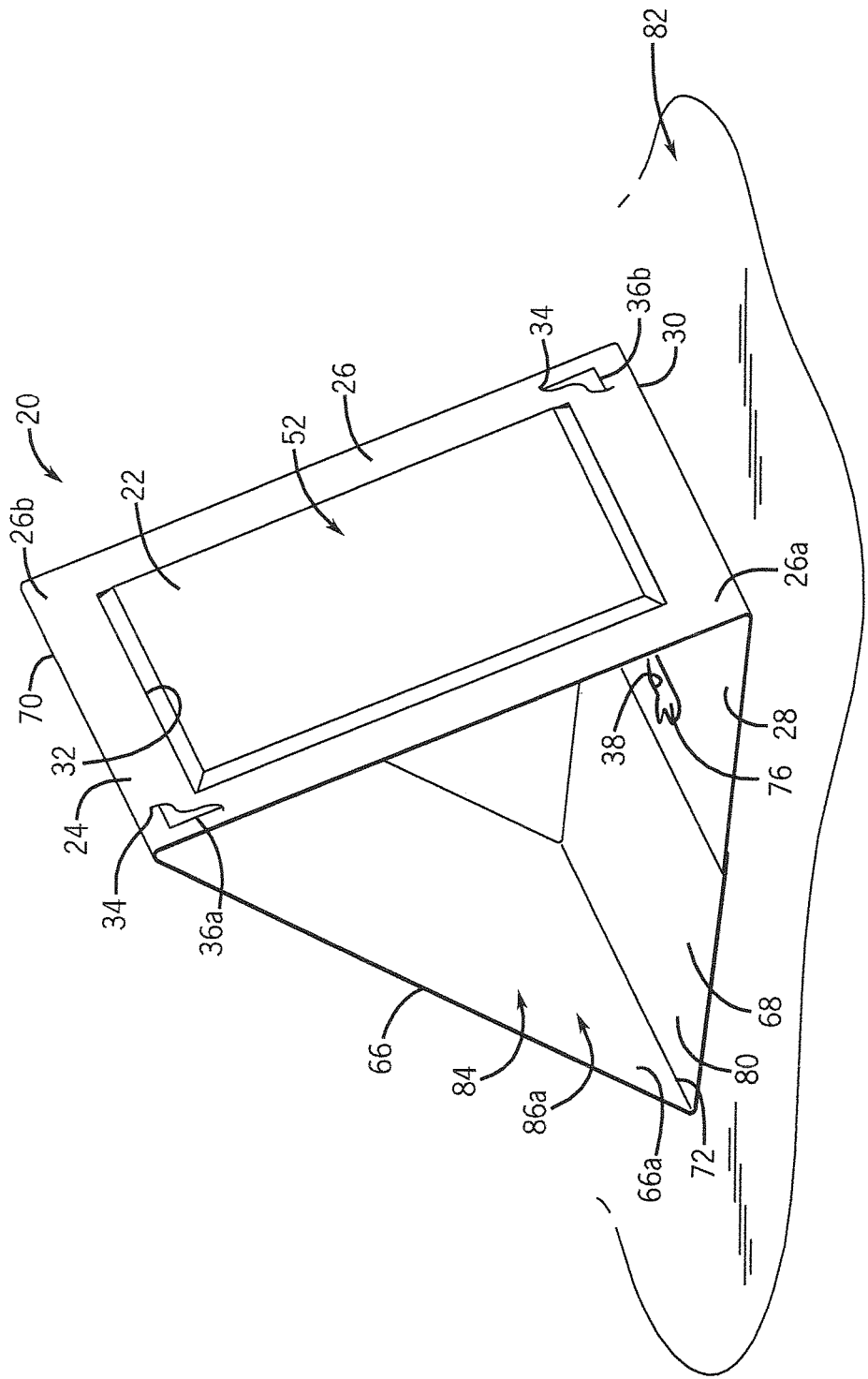
FIG. 8 is a front isometric view of the dispensing system of FIG. 1 in a second state.

In the second state, the dispensing system 20 has a substantially triangular configuration such as seen in FIG. 8. The second state is achieved by rotating the second and fourth wall portions 28 and 68, respectively, toward one another until they are nearly planar and in substantial contact with one another. The second 22 and fourth 68 wall portions are slid or otherwise positioned to allow the tab 76 to be inserted into the aperture 38 and retained therein. In the second state, the second 22 and fourth 68 wall portions form a base 80 that rests on a surface 82, thereby effectively suspending the dispenser 22 above the surface 82. Suspending the dispenser 22 facilitates emanation of the volatile material 58 contained within the volatile material dispenser 22. When activated, the permeable membrane 50 of the dispenser 22 is exposed to air within the interior space 84 of the dispensing system 20 to facilitate volatile material diffusion. Advantageously, the cup-shaped structure 52 of the dispenser 22 is viewable from an exterior of the frame 24 such that a user can see the amount of volatile material 58 remaining within the dispenser 22 upon activation.

The interior space 84 is exposed to the ambient environment through two openings 86a, 86b (only 86a is shown), which are preferably equal in size. The cross-sectional area of the openings 86a, 86b is a function of the lengths L1-4 of the first 26, second 28, third 66, and fourth 68 wall portions, respectively (see FIG. 9). The lengths L1-4 can be made larger or smaller to change the cross-sectional area of the openings 86a, 86b, to effect a greater or lesser diffusion of the volatile material 58 from the dispenser 22.

Figure 9:
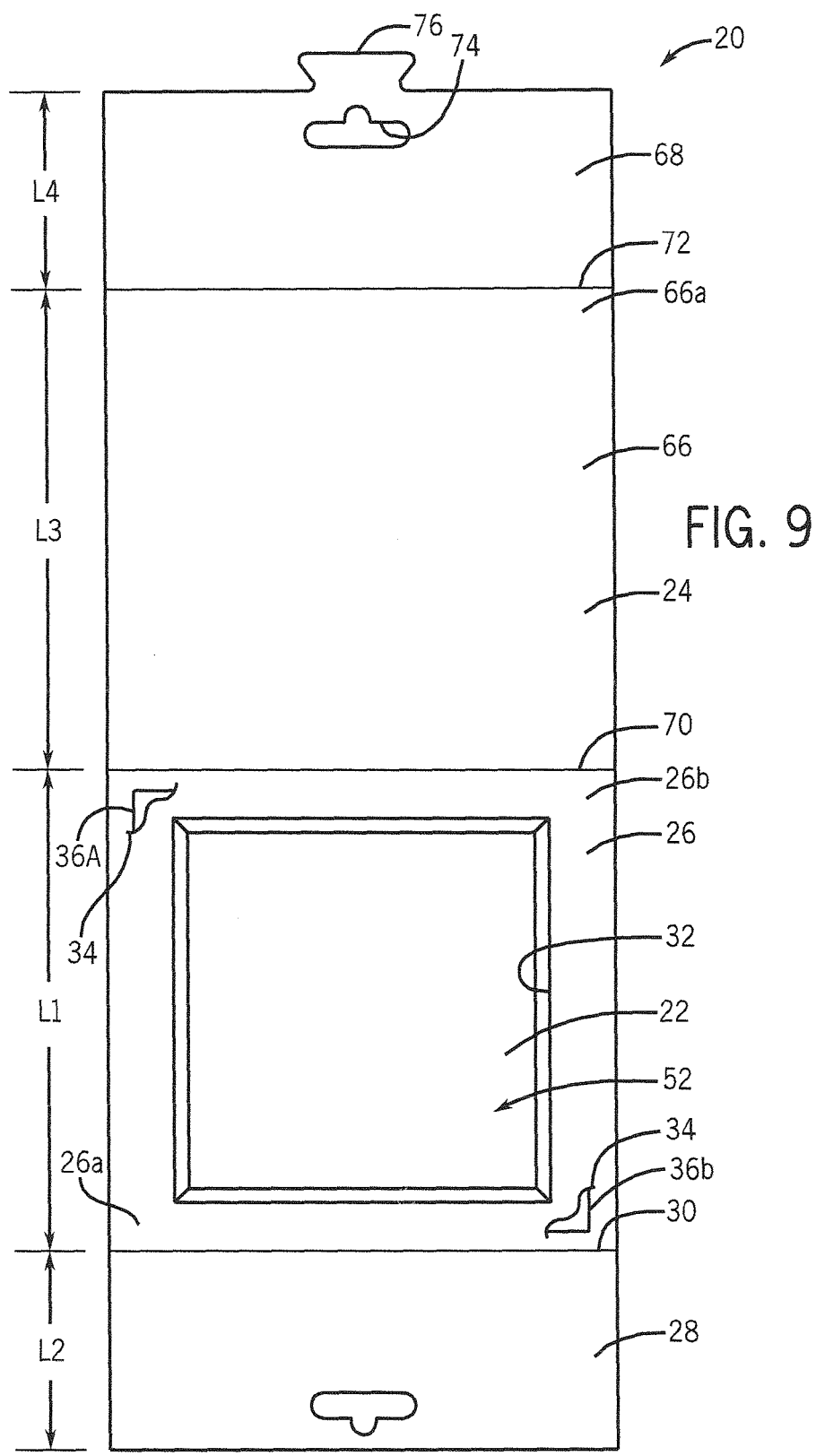
FIG. 9 is a top plan view of the frame and dispenser of FIG. 1 in an unfolded state.
Figure 10:
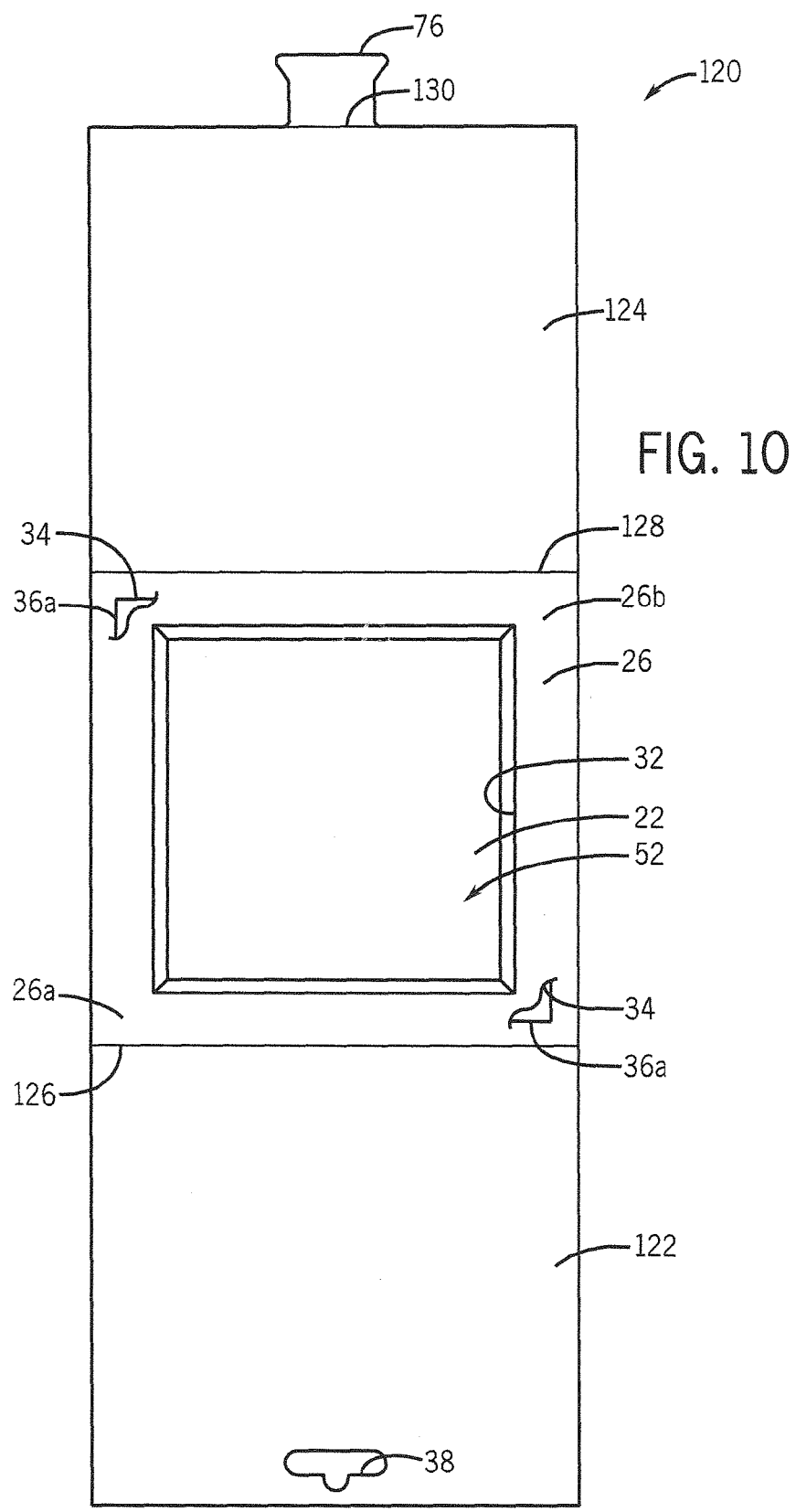
FIG. 10 is a top plan view of a second embodiment of a frame and dispenser in an unfolded state.
Figure 11:
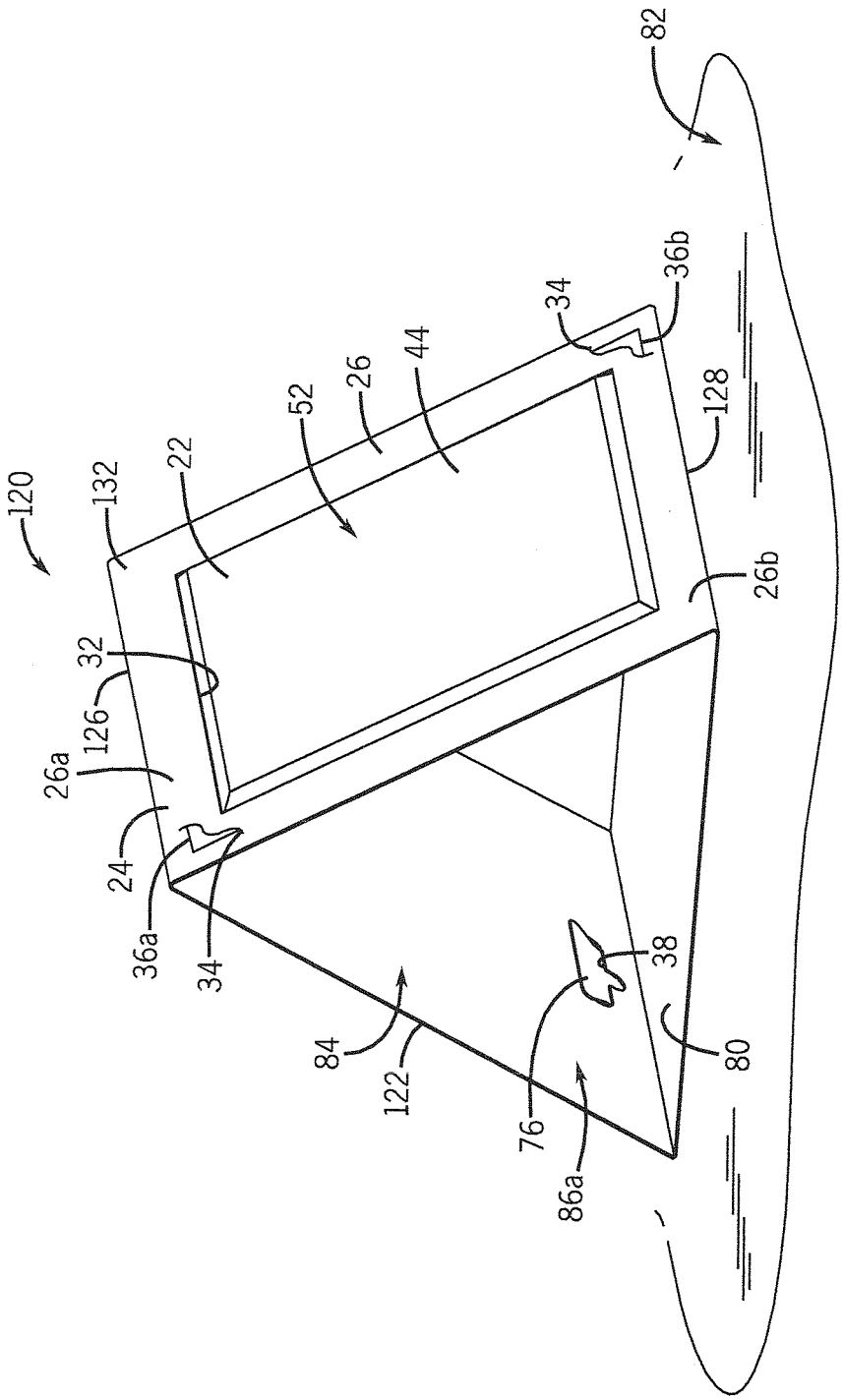
FIG. 11 is a front isometric view of the second embodiment of the dispensing system depicted in FIG. 10, which is shown in a second state.

FIGS. 10 and 11 depict a different embodiment of a dispensing system 120 similar to the dispensing system 20. However, as shown by comparing the unfolded dispensing system 20 of FIG. 9 with the unfolded dispensing system 120 of FIG. 10, it may be seen that the dispensing system 120 has only three wall portions, i.e., first 26, second 122, and third 124 wall portions. The first wall portion 26 is substantially similar to that in dispensing system 20 and houses the dispenser 22. The second wall portion 122 is connected to the first end 26a of the first wall portion 26 along fold line 126. The second wall portion 122 further includes an aperture 38. The third wall portion 124 is connected to the second end 26b of the first wall portion 26 along fold line 128 and includes a tab 76 sized to be retained within the aperture 38. The tab 76 is hingedly attached to the third wall portion 124 along fold line 130.

FIG. 11 illustrates the dispensing system 120 of FIG. 10 in the second state where it forms a substantially triangular structure similar to the dispensing system 20 of FIG. 8. Here, the second wall portion 122 and the third wall portion 124 are folded toward one another by rotating about fold lines 126 and 128, respectively, such that the blister 44 remains on the outer surface 132 of the dispensing system 120. The tab 76 is folded toward the second wall portion 122 about the fold line 130 until it is nearly planar with the second wall portion 122, at which point the tab 76 is inserted into the aperture 38 to secure the dispensing system 120 in the second state. In the second state, the third wall portion 124 forms the base 80 that rests on the surface 82.

In one embodiment, the dispensing systems 20, 120 may be sold in a package in a first state where the first 26, second 28/122, third 66/124, and optionally fourth 68 wall portions are folded together in a substantially coplanar configuration about their respective fold lines.

In a different embodiment, the dispensing systems 20, 120 are provided with openings and/or dispensers 22 of varying shapes and/or sizes. For example, the dispenser 22 and/or the cup-shaped structure 52 may be fashioned in the shape of a rectangle, circle, triangle, or other geometric shape, such as a snowflake or an animal. Further, multiple dispensers 22 may be provided in a single dispensing system 20, 120 with different or similar volatiles disposed therein.

It is also envisioned that the dispenser(s) 22 may be replaced after use, or, alternatively, the entire dispensing system 20, 120 could be thrown away as a single use dispensing system. Further, a re-usable adhesive may be used to hold some or all of the wall portions of the dispenser 22 together so that the dispenser 22 may be alternatively placed in first and second states or to facilitate the replacement of the dispenser(s) 20.

In yet another embodiment, the dispensing systems 20, 120 may be placed on a side thereof during use. In this embodiment, edges of the wall portions defining either a left or right side of the dispensing system 20, 120 are disposed adjacent the support surface 82.

Figure 13:
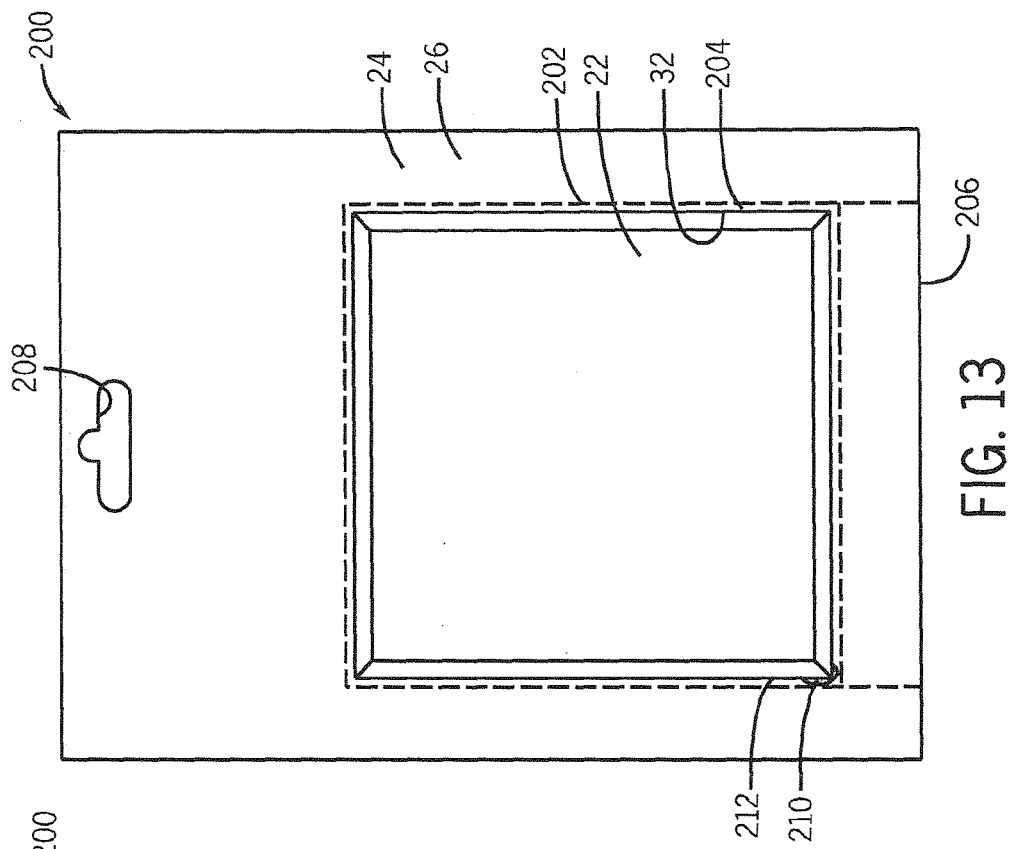
FIG. 13 is a rear elevational view of the package for a cartridge refill of FIG. 12.
Figure 12:
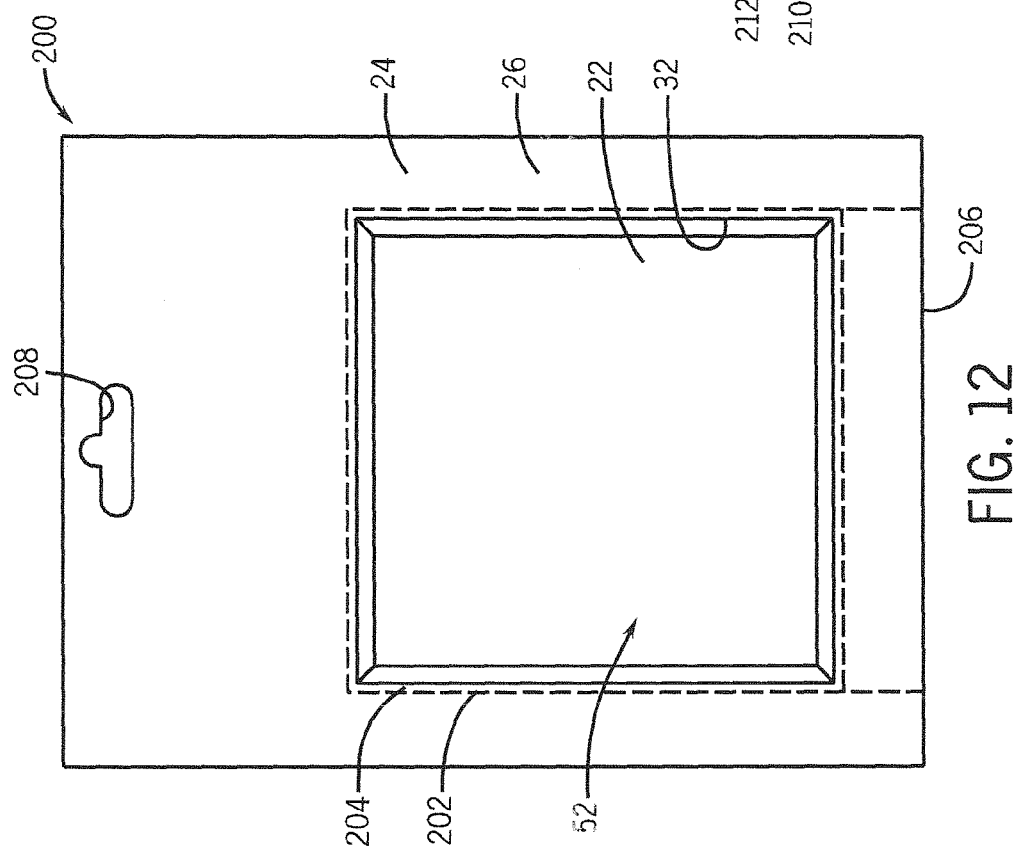
FIG. 12 is a front elevational view of a package for a cartridge refill.
Figure 14:
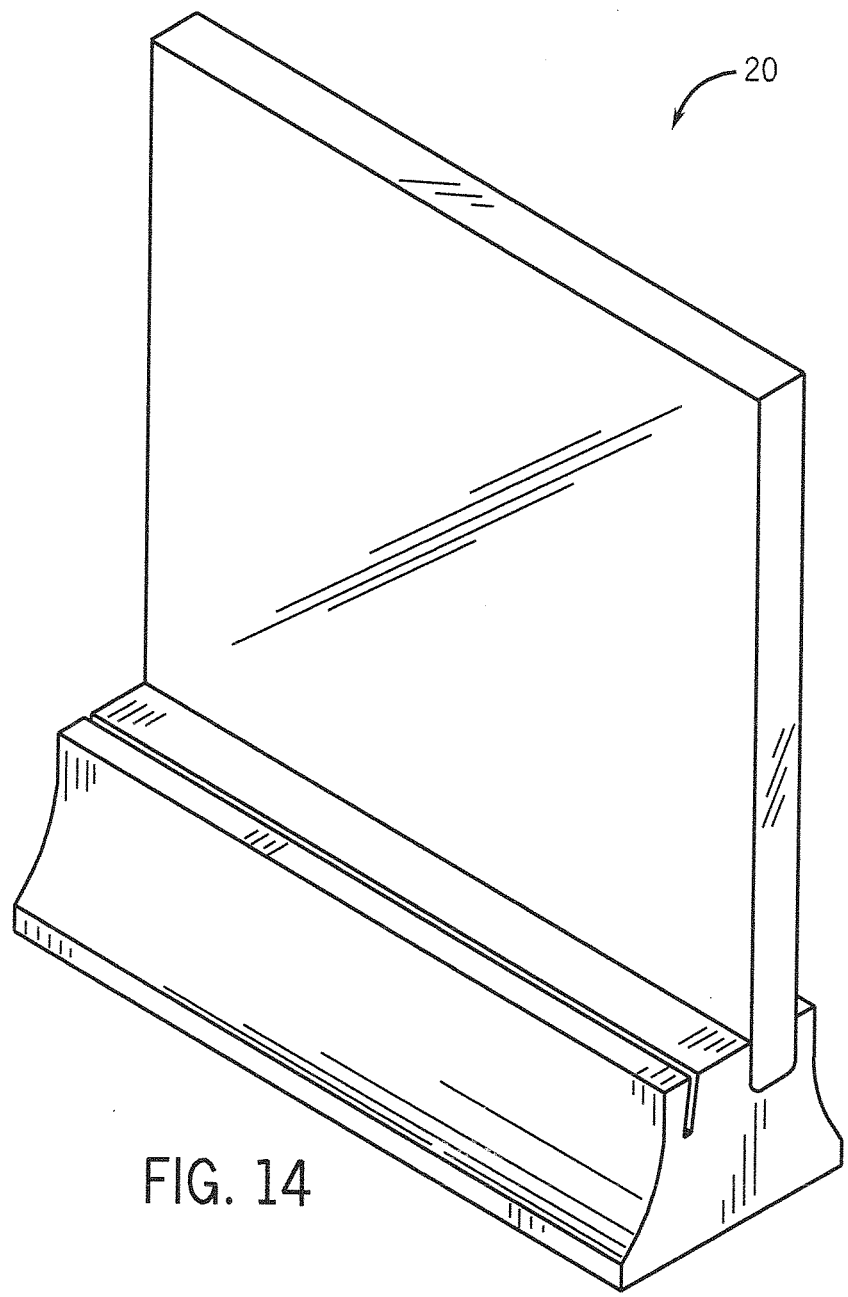
FIG. 14 is a front isometric view of another dispenser.

Referring to FIG. 12, a package 200 for a volatile material dispenser 22 is illustrated that is similar to the display frames previously discussed. The package 200 includes a volatile material dispenser or cartridge refill 22 and a display frame 24 having a wall portion 26. The cartridge refill 22 is removably attached to the display frame 24 by attachment means and disposed within an opening 32 in the display frame. Attachment means may include perforations 202 near a periphery 204 of the opening 32. In one embodiment, the perforations 202 may extend to a bottom edge 206 of the display frame 24. The wall portion 26 includes an aperture 208 shaped to permit the package 200 to be hung, for example, from a wall hanger display. When the cartridge refill 22 is removably attached to the display frame 24 by perforations 204, the cartridge refill may be adhered at one or more points 210 by an adhesive or other means to a portion 212 of the display frame 24, as shown in FIG. 13. In use, the perforations 202 may be disrupted to remove the cartridge refill 22 from the display frame 24 to be used in a separate dispenser 20, such as the one shown in FIG. 14. Exemplary embodiments of additional dispensers that the cartridge refill 22 may be used in after removal from the package 200 include those disclosed in U.S. Pat. No. 7,426,799 and U.S. patent Ser. No. 29/390,459.

The package 200 of FIGS. 12 and 13 may also serve as a dispenser for the cartridge refill 22 as shown in FIG. 15. Here, the perforations 202 on the left, right, and bottom sides, 214, 216, and 218, respectively, have been disrupted and the cartridge refill pivoted about its top side 220 to transition the display frame 24 from a substantially planar structure to a substantially non-planar structure. The three dimensional structure in this state facilitates dispensing of the volatile material 58 contained within the cartridge refill 22 when opened by increasing the surface area that may be impacted by air flowing past the structure.

Another embodiment of a package 200 is shown in FIG. 16. Here, the package 200 includes a volatile material dispenser 22 and a display frame 24. The package 200 is foldable between a first state (shown) where the system is substantially planar or flat and a second state, which is substantially triangular (see FIG. 18). The display frame 24 comprises a first wall portion 26 and a second wall portion 28 hingedly attached to a first end 26a of the first wall portion 26 by a fold line 30. The first wall portion 26 and the second wall portion 28 may be substantially rectangular in shape and may vary in size as desired. Turning to FIG. 17, an opening 32 is disposed within the first wall portion 26 as well as an aperture 208 shaped to permit the dispensing system to be hung, for example, from a wall hanger display. The second wall portion 28 also includes an aperture 226 shaped similarly to the aperture 208.

In the present embodiment, the dispenser 22 is fittingly retained within the opening 32 of the frame 24 by an adhesive 222 at one or more attachment points 224. Preferably, an adhesive 222 may be chosen that enables a user to easily remove the cartridge refill 22 from the display frame 24 for use in a separate dispenser. Moreover, the adhesive 222 may function to adhere the first 26 and second 28 wall portions to one another to maintain the package in the first state until use, as seen in FIG. 16.

Figure 18:
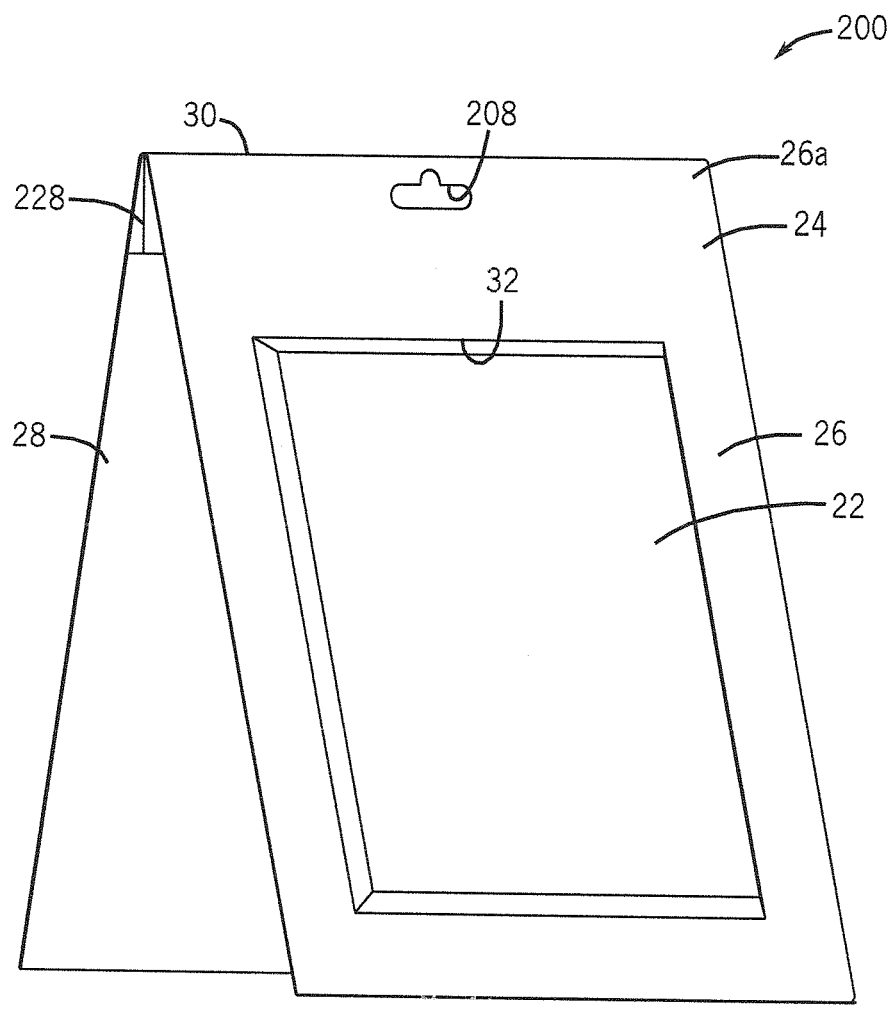
FIG. 18 is a front isometric view of the package depicted in FIG. 16, which is shown in a second state.

Moreover, the packages 200 of the present disclosure may be constructed of a cellulosic material, a plastic material, and combinations thereof, that have sufficient rigidity to maintain the display frame 24 in the second state, as seen in FIGS. 15 and 18. Another possible retention means includes a foldable truss 228 that extends from the first wall portion 26 to the second wall portion 28 near the fold line 30 to maintain the display frame 24 in the second state (see FIG. 18).

Figure 19:
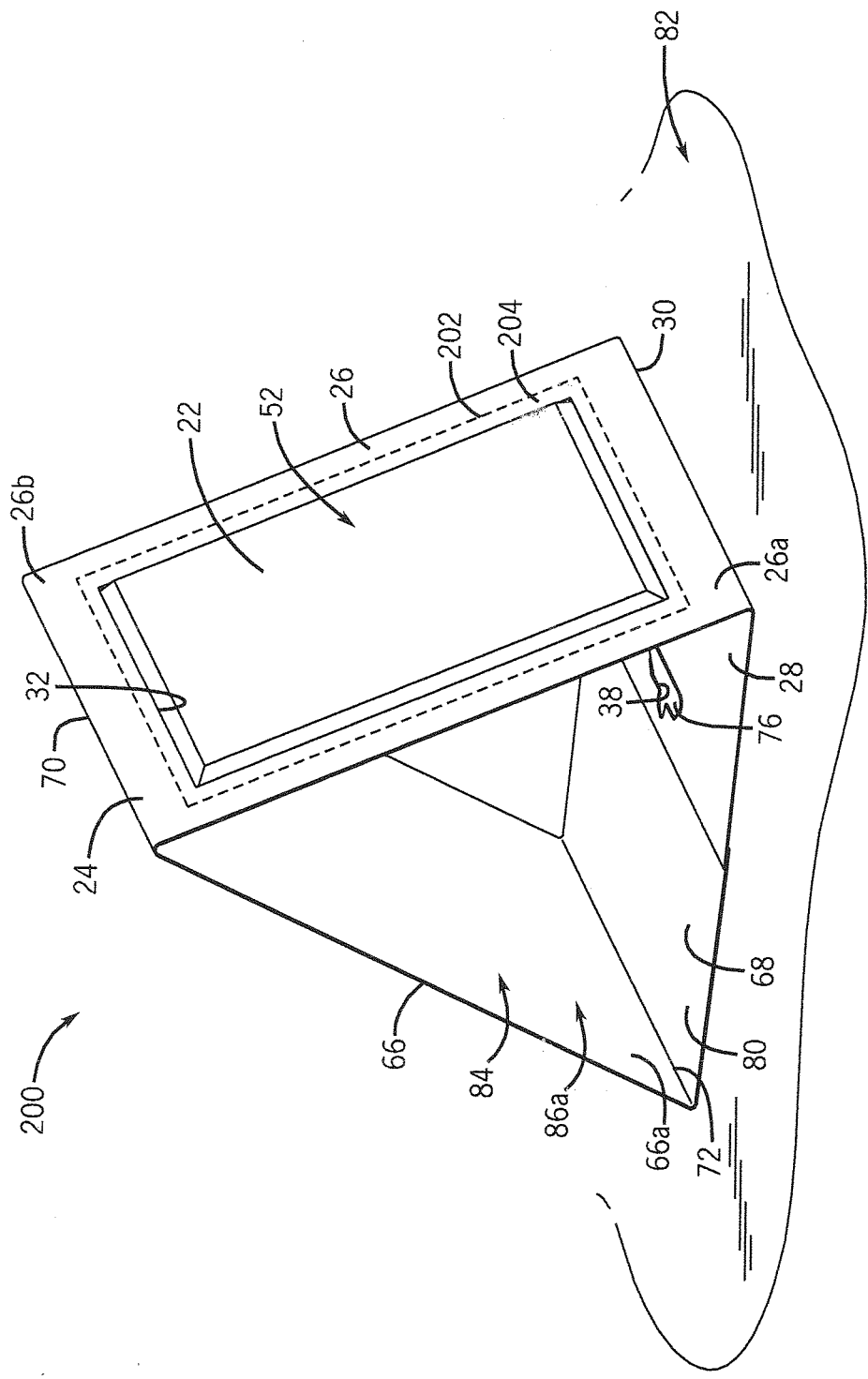
FIG. 19 is a front isometric view of a package in a second state similar to the dispensing system of FIG. 8.
Figure 20:
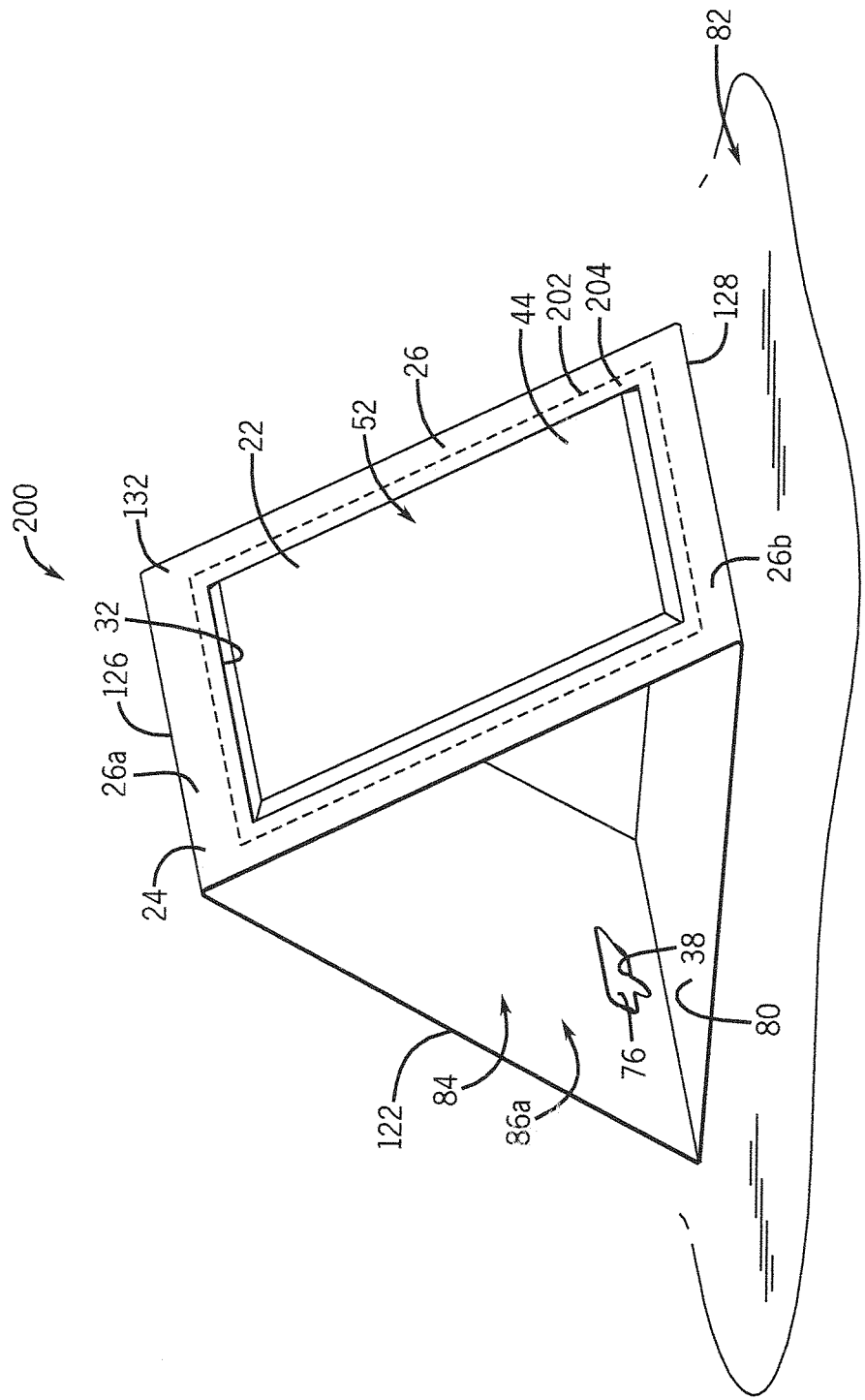
FIG. 20 is a front isometric view of a package in a second state similar to the dispensing system of FIG. 11.

Additional packages 200 contemplated herein are variations of the four and three panel dispensing systems disclosed above. For example, FIGS. 19 and 20 illustrate display frames 24 similar to those in FIGS. 8 and 11, respectively, with the exception that the cartridge refill 22 is removable from the display frame by disrupting perforations 202 around the periphery 204 of the opening 32.

Similarly, the packages 200 shown in FIGS. 21 and 22 (views in an unfolded state) approximate the four and three panel dispensing systems as shown in FIGS. 9 and 10, respectively, with the exception that the cartridge refills 22 are attached to the display frames 24 by an adhesive 222 at attachment points 224. Here, the adhesive 222 also serves to removably secure the packages 200 in a substantially planar first state, similar to that illustrated in FIG. 16. For the package illustrated in FIG. 21, the package may fold along fold line 70 to achieve a substantially planar configuration. For the package illustrated in FIG. 22, the first 26 and third 124 wall portions first fold together along fold line 128. Subsequently, the second wall portion 122 folds onto the third wall portion 124 along fold line 126 to form a substantially planar structure.

Those skilled in the art will appreciate the numerous variations that may be made with respect to the present disclosure and which is intended to be captured herein. Other embodiments include all of the various combinations of individual features of each of the embodiments described herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

The air freshener dispensing system described herein advantageously combines the functional and aesthetic characteristics of a display frame that is adjustable between first and second states to facilitate the use of the system.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A package for a refill for dispensing a volatile material, comprising:
    a wall portion with an opening disposed therein;
    a cartridge refill disposed within the opening; and
    attachment means that removably attaches the cartridge refill to the wall portion,
    wherein the wall portion and the cartridge refill form a substantially planar structure in a first state,
    wherein partial disruption of the attachment means partially removes the cartridge refill from the wall portion to create a substantially non-planar structure in a second state to facilitate dispensing a volatile material from the cartridge refill, and
    wherein in the second state, the wall portion defines a first leg and the cartridge refill itself acts as a second leg.

2. The package of claim 1, wherein the wall portion comprises a pressed cellulose material.

3. The package of claim 1, wherein the wall portion further comprises an aperture.

4. The package of claim 1, wherein the attachment means comprise at least one of mechanical means or chemical means.

5. The package of claim 1, wherein the attachment means comprises a plurality of attachment points.

6. The package of claim 1, wherein the substantially non-planar structure comprises a substantially triangular structure.

7. The package of claim 1, wherein the cartridge refill comprises a blister holding a volatile material and a permeable membrane extending across an open end of the blister.

8. A package for a refill for dispensing a volatile material, comprising:
    a wall portion with an opening disposed therein;
    a cartridge refill disposed within the opening; and
    attachment means that removably attaches the cartridge refill to the wall portion,
    wherein the wall portion and the cartridge refill form a substantially planar structure in a first state,
    wherein partial disruption of the attachment means partially removes the cartridge refill from the wall portion to create a substantially non-planar structure in a second state to facilitate dispensing a volatile material from the cartridge refill, and
    wherein in the second state, the wall portion defines a first leg, the cartridge refill itself acts as a second leg, and a bottom of the cartridge refill rests on a support surface.

9. The package of claim 8, wherein the wall portion comprises a pressed cellulose material.

10. The package of claim 8, wherein the wall portion further comprises an aperture.

11. The package of claim 8, wherein the attachment means comprise at least one of mechanical means or chemical means.

12. The package of claim 8, wherein the attachment means comprises a plurality of attachment points.

13. The package of claim 8, wherein the substantially non-planar structure comprises a substantially triangular structure.

14. The package of claim 8, wherein the cartridge refill comprises a blister holding a volatile material and a permeable membrane extending across an open end of the blister.

* * * * *